(12) United States Patent
Quax et al.

(10) Patent No.: US 7,037,714 B2
(45) Date of Patent: *May 2, 2006

(54) **EXPRESSION VECTORS ENCODING *BACILLUS SUBTILIS* DISULFIDE BOND ISOMERASE AND METHODS OF SECRETING PROTEINS IN GRAM-POSITIVE MICROORGANISMS USING THE SAME**

(75) Inventors: Wilhelmus J. Quax, Kropswolde (NL); Robert M. Caldwell, Belmont, CA (US)

(73) Assignee: Genencor International, Inc., Palo Alto, CA (US)

( * ) Notice: Subject to any disclaimer, the term of this patent is extended or adjusted under 35 U.S.C. 154(b) by 506 days.

This patent is subject to a terminal disclaimer.

(21) Appl. No.: 10/339,278

(22) Filed: Jan. 9, 2003

(65) Prior Publication Data

US 2003/0124676 A1    Jul. 3, 2003

Related U.S. Application Data

(63) Continuation of application No. 09/462,842, filed as application No. PCT/US98/14704 on Jul. 15, 1998, now Pat. No. 6,521,421.

(30) Foreign Application Priority Data

Jul. 16, 1997    (EP)    ................... 97305288

(51) Int. Cl.
| | |
|---|---|
| *C12N 15/61* | (2006.01) |
| *C12N 15/63* | (2006.01) |
| *C12N 1/21* | (2006.01) |
| *C12N 9/90* | (2006.01) |
| *C12N 9/02* | (2006.01) |
| *C07H 21/04* | (2006.01) |

(52) U.S. Cl. .............. 435/320.1; 435/252.3; 435/252.31; 435/233; 435/189; 536/23.2

(58) Field of Classification Search ............... 435/233, 435/252.3, 252.31, 320.1, 189; 536/23.2
See application file for complete search history.

(56) References Cited

U.S. PATENT DOCUMENTS

| | | | |
|---|---|---|---|
| 3,817,837 A | 6/1974 | Rubenstein et al. | 195/103.5 |
| 3,850,752 A | 11/1974 | Schuurs et al. | 195/103.5 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,816,567 A | 3/1989 | Cabilly et al. | 530/387 |
| 5,496,719 A | 3/1996 | Yamada et al. | 435/233 |

FOREIGN PATENT DOCUMENTS

| | | |
|---|---|---|
| EP | 0 293 793 A2 | 7/1988 |
| EP | 0 293 793 A3 | 7/1988 |
| EP | 0 277 563 A1 | 10/1988 |
| WO | WO 93/25676 | 12/1993 |
| WO | WO 94/08012 | 4/1994 |

OTHER PUBLICATIONS

Ausubel et al., *Current Protocols in Molecular Biology*, John Wiley & Sons, Inc. Ch. 2 and 3, 1987.

Bakhei et al., "Studies on Transfection and Transformation of Protoplasts of *Bacillus larvae, Bacillus subtilis*, and *Bacillus popilliae*," Applied and Environmental Microbiology, vol. 49, No. 3, pp. 577-581, Mar., 1985.

Chang et al., "High Frequency Transformation of *Bacillus subtilis* Protoplasts by Plasmid DNA," *Molec. Gen. Genet.*, vol. 168, pp. 111-115, 1979.

Contente et al., "Marker Rescue Transformation by Linear Plasmid DNA in *Bacillus subtilis*," *Plasmid*, vol. 2, pp. 555-571, 1979.

Fischer et al., "Introduction of plasmid pC194 into *Bacillus thunngiensis* by protoplast transformation and plasmid transfer," *Archives of Microbiology*, vol. 139, pp. 213-217, 1984.

Haima et al., "Novel plasmid marker rescue transformation system for molecular cloning in *Bacillus subtilis* enabling direct selection of recombinants," *Mol. Gen. Genet.*, vol. 223, pp. 185-191, 1990.

Holubova et al., "Transfer of Liposome-Encapsulated Plasmid DNA to *Bacillus subtilis* Protoplasts and Calcium-Treated *Escherichia coli* Cells," *Folia Microbiol.*, vol. 30, pp. 97-100, 1985.

(Continued)

*Primary Examiner*—Elizabeth Slobodyansky
(74) *Attorney, Agent, or Firm*—Genencor International, Inc.

(57) ABSTRACT

The present invention relates to nucleic acid sequences and amino acid sequences for *Bacillus subtilis* disulfide bond isomerases, Dsb1 and Dsb2 and methods for increasing the secretion of heterologous and homologous proteins in Gram-positive microorganisms.

12 Claims, 7 Drawing Sheets

OTHER PUBLICATIONS

Harti et al., "Molecular chaperones in cellular protein folding," *Structural Biology*, vol. 5, pp. 92-102, 1995.

Ishihara et al., "Cloning and Characterization of the Gene for a Current Opinion in Protein Thiol-Disulfide Oxidoreductase in *Bacillus brevis*," *J. of Bacteriology*, vol. 177, No. 3, pp. 745-749, 1995.

Kroll et al., "A Multifunctional Prokaryotic Protein Expression System: Overproduction, Affinity Purification, and Selective Detection," *DNA and Cell Biology*, vol. 12, No. 5, pp. 441-453, 1993.

Maddox et al., "Elevated Serum Levels in Human Pregnancy of a Molecule Immunochemically Similar to Eosinophil Granule Major Basic Protein," *J. Exp. Med.*, vol. 158, pp. 1211-1228, Oct., 1983.

Mann et al., "Transformation of *Bacillus spp.*: an Examination of the Transformation of *Bacillus* Protoplasts by Plasmids pUB110 and pHV33," *Current Microbiology*, vol. 13, pp. 191-195, 1986.

McDonald et al., "Plasmid Transformation of *Bacillus sphaericus* 1593," *J. General Microbiology*, vol. 130, pp. 203-208, 1984.

Murray et al., "Codon usage in plant genes," Nucleic Acids Research, vol. 17, No. 2, pp. 477-498, 1989.

Porath, "Immobilized Metal Ion Affinity Chromatography," *Protein Expression and Purification*, vol. 3, pp. 263-281, 1992.

Smith et al., "Protoplast Transformation in Coryneform Bacteria and Introduction of an α-Amylase Gene from *Bacillus amyloliquefaciens* into *Brevibacaterium lactofermentum*," *Applied and Environmental Microbiology*, vol. 51, No. 3, pp. 634-639, Mar., 1986.

Vorobjeva, et al., "Transformation of *Bacillus Megaterium* Protoplasts by Plasmid DNA," *FEMS Microbiology Letters* 7, pp. 261-263, 1980.

Weinrauch et al., "Plasmid Marker Rescue Transformation in *Bacillus subtilis*," *Journal of Bacteriology*, vol. 154, No. 3, pp. 1077-1087, Jun., 1983.

Weinrauch et al., "Plasmid Market Rescue Transformation Proceeds by Breakage-Reunion in *Bacillus subtilis*," *J. of Bacteriology*, vol. 169, No. 3, pp. 1205-1211, 1987.

```
                10                            30
atgaatacaagatatgtaaaatcattttttttattactgttttttctc
 M  N  T  R  Y  V  K  S  F  F  L  L  L  F  F  L 50                         70                           90
tctttctttggcacaatggctagtttattctacagtgagatcatgcat
 S  F  F  G  T  M  A  S  L  F  Y  S  E  I  M  H 110                      130
ttcaaaccatgtgttctatgttggtatcaaagaatatttctatatcct
 F  K  P  C  V  L  C  W  Y  Q  R  I  F  L  Y  P 150                     170                       190
ataccattatcttactaataggcttattaaaaaagatcttaattcg
 I  P  I  I  L  L  I  G  L  L  K  K  D  L  N  S 210                         230
atattttatgttgttttcctttcatcaattggattgattattgcgttt
 I  F  Y  V  V  F  L  S  S  I  G  L  I  I  A  F 250                          270                        2
tatcattatattatccaacttacacaaagcaaaagtgtcgtatgtgaa
 Y  H  Y  I  I  Q  L  T  Q  S  K  S  V  V  C  E 90                           310                          330
attggaaccaacagctgcgcaaaaattgaagtagagtatctaggcttt
 I  G  T  N  S  C  A  K  I  E  V  E  Y  L  G  F 350                       370
attacattacccttaatgagttcagtatgttttgcattgatatttggt
 I  T  L  P  L  M  S  S  V  C  F  A  L  I  F  G 390                       410                       430
ataggactgaaattaattatcaaaagcaagaaattaaaacaaaatcaa
 I  G  L  K  L  I  I  K  S  K  K  L  K  Q  N  Q catgtatataat
 H  V  Y  N
```

FIG._1

```
ecodsbb.pl       MLRFLNQCSQGRGAWLLMAFTALALALELTALWFQHVMLLKPCVLCIYERCALFGVLGAALI
                      ·|: ·· ::|::| |||||·||··|·|·· |·· ||
YOLK             MNTRYVKSFFLLLFFLSFFGTMASLFYSEIMHFKPCVLCWYQRIFLYPIPILLI
                              10        20        30        40        50 ecodsbb.pl       GAIAPKTPLRYVAMVIWLYSAFRGVQLTYEHTMLQLYPSPFATCDFMVRFPEWLPLDKWV
                 |·:  |   |·  ·|·|| |·  |:·|  |·  ::|::||   ·|
YOLK             GLL--KKDLNSIFYVVFLSSI--GLIIAFYHYIIQLTQSKSVVCEIGTNSCAKIEVEYLG
                        60        70        80        90       100       110 ecodsbb.pl       PQVFVASGDCAERQWDFLGLEMPQWLLGIFIAYLIVAVLVVISQPFFAKKKRDLFGR
                                                               ↑
YOLK             FITLPLMSSVCFALIFPGIGLKLIIKSKKLKQNQHVYN
                      120       130       140
```

FIG._2

```
ecodsbb.pl   MLRFLNQCSQGRGAWLLMAFTALALELTALWFQHVMLLKPCVLCIYERCALFGVLGAALI
                                      ||  :|:::  :  ||||  ||||   |:   |
YVGU         MKNRIVFLYASWVVALIAMLGSLYFSEIRKFIPCELCWYQRILMYPLVLILGI
             10        20        30        40        50 ecodsbb.pl   GAIAPKTPLRYVAMVIWLYSAFRGVQLTYEHTMLQLYPSPFATCDFMVRFPEWLPLDKWV
             ::: :  ::  ::       ||:                |: :|||||||
YVGU         ATFQGDTRVKKYVLPMAIIGAF----ISIMHYLEQKVPGFSGIKPCVSGVPCSGQYINWF
             60        70        80        90       100 ecodsbb.pl   PQVFVASGDCAERQWDFLGLEMPQWLLGIFIAYLIVAVLVVISQPFKAKKRDLFGR
YVGU         GFITIPFLALIAFILIIFMCLLKGEKSE
             110       120       130
```

FIG._3

```
YOLK  MNTRYVKSFFLLLFFLSFFGTMASLFYSEIMHFKPCVLCWYQRIFLYPIPILLIGLLKK
          :::|:  |: :  ::::|||  ::|| |||  |:::|| ||||:|::  :|| :: |::
YVGU  MKNRIV--FLYASWVVALIAMLGSLYFSEIRKFIPCELCWYQRILMYPLVLILGIATFQG
             10        20        30        40        50

YOLK  DLNSIFYVVFLSSIGLIIAFYHYIIQLTQSKSVV--CEIGTNSCAKIEVEYLGFITLPLM
         ||:: ||:||:: |||  ::|:::|:  |:   |  |: |     |: :::|||||:||:
YVGU  DTRVKKYVLPMAIGAFISIMHYLEQKVPGFSGIKPCVSGV-PCSGQYINWFGFITIPFL
             70        80        90       100       110

YOLK  SSVCFALIFGIGLKLIIKSKKLKQNQHVYN
          :: |||||| || ||  |:  :|::|
YVGU  ALIAFILI--IIFMCLLKGEKSE
             120       130

FIG._4
```

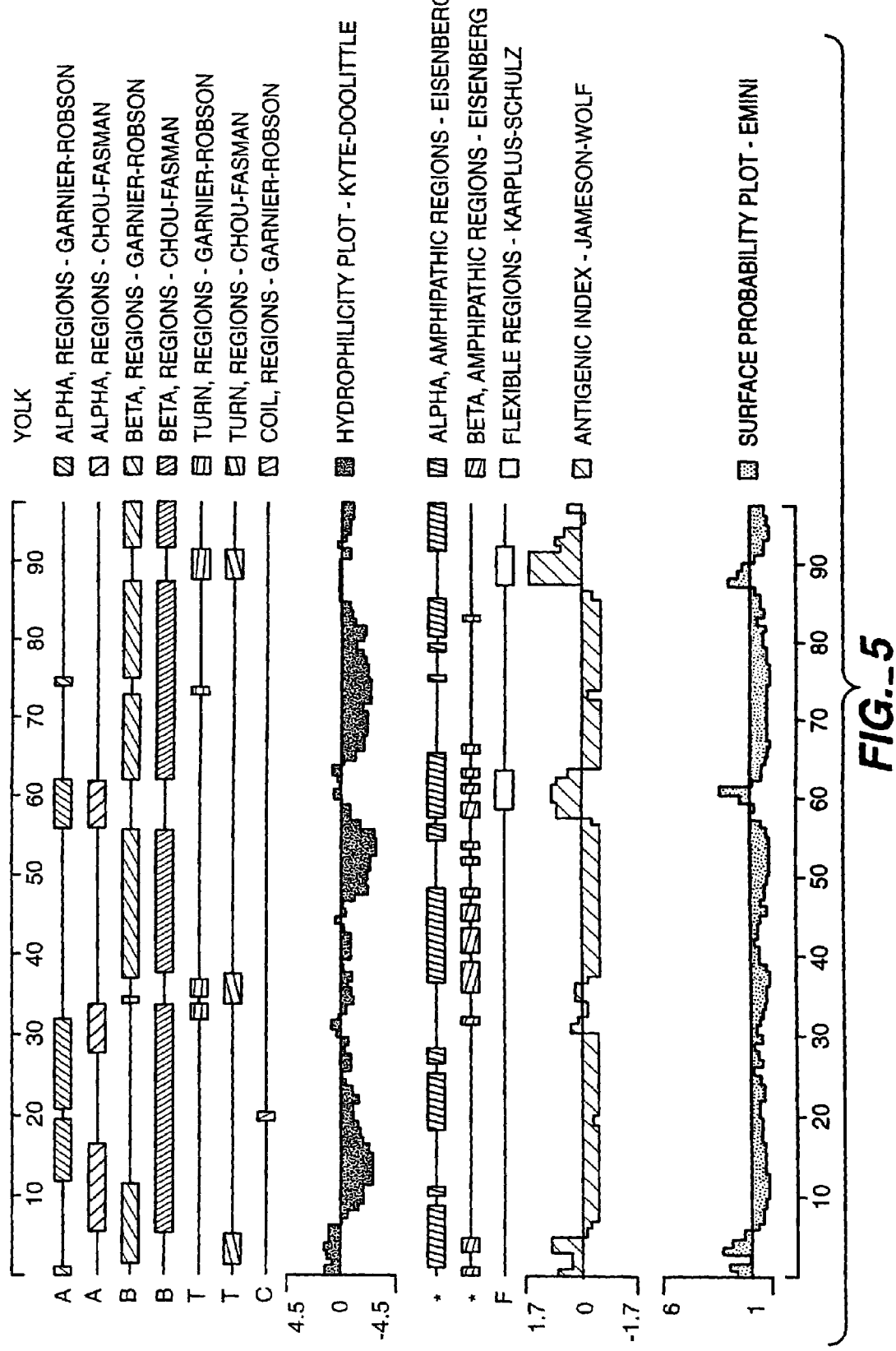
FIG._5

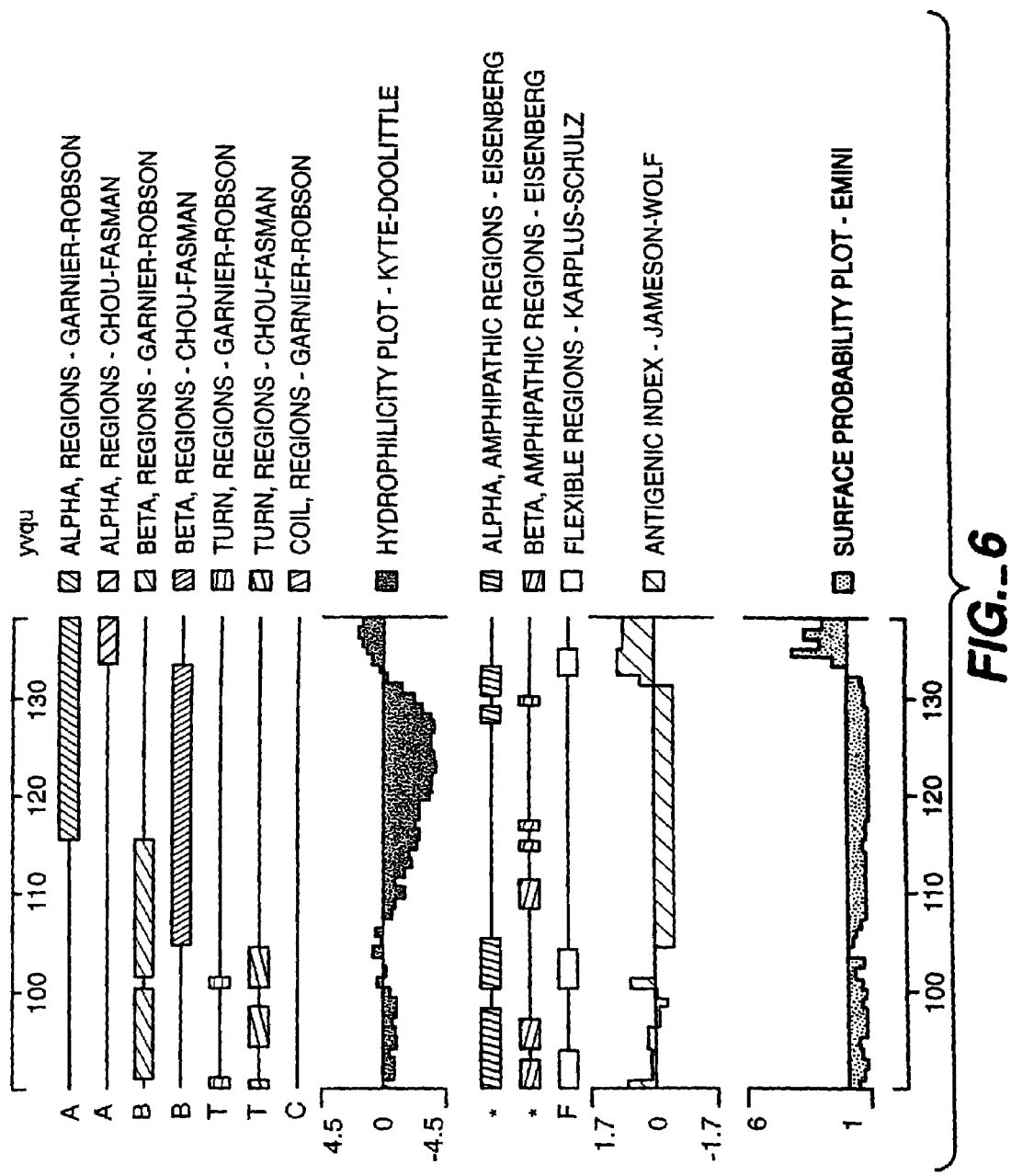
FIG._6

```
          10                            30
atgaaaaatagaatcgtattttatatgcttcctggggttgtggctctt
 M   K   N   R   I   V   F   L   Y   A   S   W   V   V   A   L 50                  70                          90
atcgctatgctgggcagcctgtatttcagtgaaatcagaaagtttatt
 I   A   M   L   G   S   L   Y   F   S   E   I   R   K   F   I 110                       130
ccatgtgaactgtgctggtaccagcgtatcctcatgtatccgctcgtc
 P   C   E   L   C   W   Y   Q   R   I   L   M   Y   P   L   V 150                       170                      190
ctgattttaggcatcgccacctttcaaggggacacacgagtgaaaaaa
 L   I   L   G   I   A   T   F   Q   G   D   T   R   V   K   K 210                      230
tatgtgctcccgatggcgattattggggcattcatttcgatcatgcat
 Y   V   L   P   M   A   I   I   G   A   F   I   S   I   M   H 250                      270                        2
tacttagagcaaaaagtgcccggctttagcggcattaagccatgtgtc
 Y   L   E   Q   K   V   P   G   F   S   G   I   K   P   C   V 90                       310                       330
agcggcgtgccgtgctcgggccaatatattaactggtttggtttatt
 S   G   V   P   C   S   G   Q   Y   I   N   W   F   G   F   I 350                       370
acgattccattcctggccctgattgcttttatcctgattatcattttt
 T   I   P   F   L   A   L   I   A   F   I   L   I   I   F 390                 410
atgtgcctgctgaaaggcgaaaaatctgaa
 M   C   L   L   K   G   E   K   S   E
```

EXPRESSION VECTORS ENCODING *BACILLUS SUBTILIS* DISULFIDE BOND ISOMERASE AND METHODS OF SECRETING PROTEINS IN GRAM-POSITIVE MICROORGANISMS USING THE SAME

This is a Continuation of U.S. patent application Ser. No. 09/462,842, filed on Mar. 22, 2000 now U.S. Pat. No. 6,521,421, which is a national stage of PCT/US98/14704, filed on Jul. 15, 1998.

FIELD OF THE INVENTION

The present invention generally relates to expression of proteins in gram-positive microorganisms and specifically to gram positive microorganism disulfide bond isomerases. The present invention provides expression vectors, methods and systems for the production of proteins in gram-positive microorganisms.

BACKGROUND OF THE INVENTION

Gram-positive microorganisms, such as members of the group *Bacillus*, have been used for large-scale industrial fermentation due, in part, to their ability to secrete their fermentation products into the culture media. In gram-positive bacteria, secreted proteins are exported across a cell membrane and a cell wall, and then are subsequently released into the external media usually obtaining their native conformation.

The folding of polypeptide chains depends upon the assistance of molecular chaperones and folding catalysts, such as disulfide bond isomerases, which accelerate specific steps in folding. (Hart) et al., 1995, Current Opinion in Structural Biology, 5:92–102). Disulfide bond isomerases can covalently modify proteins by catalyzing specific isomerization steps that may limit the folding rate of some proteins (PCT/US93/09426).

Disulfide bond isomerase catalyzes thiol/disulfide interchange reactions and promotes disulfide formation, isomerization or reduction, thereby facilitating the formation of the correct disulfide pairings, and may have a more general role in the prevention and premature misfolding of newly translocated chains. Disulfide bond isomerase interacts directly with newly synthesized secretory proteins and is required for the folding of nascent polypeptides in the endoplasmic reticulum (ER) of eukaryotic cells.

In spite of advances in understanding portions of the protein secretion machinery in procaryotic cells, the complete mechanism of protein secretion and the mechanisms associated with correct folding of secreted proteins, especially for gram-positive microorganisms has yet to be fully elucidated.

SUMMARY OF THE INVENTION

The capacity of the secretion machinery of a Gram-positive microorganism may become a limiting factor or bottleneck to the secretion of properly folded proteins or polypeptides and the production of proteins having the correct conformation in secreted form, in particular when the proteins are recombinantly introduced and overexpressed by the host cell. The present invention provides a means for alleviating that bottle neck.

The present invention is based, in part, upon the discovery of a *Bacillus subtilis* disulfide bond isomerases, Dsb1 and Dsb2, identified in heretofore uncharacterised translated genomic DNA by their overall amino acid homology with an *E. coli* disulfide bond isomerase. For *E. coli* disulfide bond isomerase having accession number P30018 and ID number DSBB_ECOLI, it was noted that cysteine residues at 41, 44, 104 and 130 were essential for activity. Those residues are conserved in *B. subtilis* Dsb1 and Dsb2 and noted in FIGS. 2, 3 and 4. The present invention is also based upon the overall structural homology that Dsb1 and Dsb2 have with each other. The present invention is also based in part on the presence in of potential transmembrane spanning regions in Dsb1 and Dsb2.

The present invention provides isolated nucleic acid and amino acid sequences for *B. subtilis* Dsb1 and Dsb2. The amino acid sequence for *B. subtilis* Dsb1 and Dsb2 are shown in FIGS. 1 and 7, respectfully. The nucleic acid sequences encoding *B. subtilis* Dsb1 and Dsb2 are the polynucleotide sequences shown in FIGS. 1 and 7, respectfully.

The present invention also provides improved methods for secreting correctly folded proteins from gram-positive microorganisms. Accordingly, the present invention provides an improved method for secreting a protein in a gram-positive microorganism comprising the steps of obtaining a gram-positive microorganism host cell comprising nucleic acid encoding Dsb1 and/or Dsb2 wherein said nucleic acid is under the control of expression signals capable of expressing said disulfide bond isomerase in a gram-positive microorganism said microorganism further comprising nucleic acid encoding said protein; and culturing said microorganism under conditions suitable for expression of said disulfide bond isomerase and expression and secretion of said protein. In one embodiment of the present invention, the protein is homologous or naturally occurring in the gram-positive microorganism. In another embodiment of the present invention, the protein is heterologous to the gram-positive microorganism.

The present invention provides expression vectors and host cells comprising isolated nucleic acid encoding a gram-positive Dsb1 and/or Dsb2. In one embodiment of the present invention, the host cell comprising nucleic acid encoding Dsb1 or Dsb2 is genetically engineered to produce a desired protein, such as an enzyme, growth factor or hormone. In yet another embodiment of the present invention, the enzyme is selected from the group consisting of proteases, carbohydrases including amylases, cellulases, xylanases, reductases and lipases; isomerases such as racemases, epimerases, tautomerases, or mutases; transferases, kinases and phophatases acylases, amidases, esterases, oxidases. In a further embodiment the expression of the disulfide bond isomerases Dsb1 and/or Dsb2 is coordinated with the expression of other components of the secretion machinery. Preferably other components of the secretion machinary, i.e., translocase, SecA, SecY, SecE and/or other secretion factors known to those of skill in the art are modulated in expression at an optimal ratio to Dsb1 and Dsb2. For example, it may be desired to overexpress multiple secretion factors in addition to Dsb1 or Dsb2 for optimum enhancement of the secretion patterns.

The present invention also provides a method of identifying homologous non *Bacillus subtilis* Dsb1 and Dsb2 that comprises hybridizing part or all of dsb1 and dsb2 nucleic acid shown in the Figures with nucleic acid derived from gram-positive microorganisms. In one embodiment, the nucleic acid is of genomic origin. In another embodiment, the nucleic acid is a cDNA. The present invention encompasses novel gram-positive microorganism disulfide bond isomerases identified by this method.

BRIEF DESCRIPTION OF THE DRAWINGS

FIG. 1 shows the nucleic acid (SEQ ID NO: 1) and deduced amino acid sequence for Dsb1 (SEQ ID NO: 2).

FIG. 2 shows an amino acid alignment of *E. coli* disulfide bond isomerase (SEQ ID NO: 3) with the deduced amino acid sequence for Dsb1 (YOLK). The cysteine residues equivalent to *E. coli* cysteine residues at 41, 44, 104 and 130 found to be essential for activity of the *E. coli* disulfide bond isomerase are marked in FIGS. 2, 3 and 4.

FIG. 3 shows an amino acid alignment of *E. coli* DSB (SEQ ID NO: 3) vs Dsb 2 (YVGU) (SEQ ID NO: 5).

FIG. 4 shows an amino acid alignment of Dsb1 (YOLK) vs Dsb2 (YVGU).

FIG. 5 shows a hydrophilicity plot for Dsb1 (YOLK).

FIG. 6 shows a hydrophilicity plot of Dsb 2 (YVGU).

FIG. 7 shows the nucleic acid (SEQ ID NO: 4) and deduced amino acid sequence for Dsb2 (SEQ ID NO: 5).

DETAILED DESCRIPTION

Definitions

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

The present invention encompasses novel Dsb1 and Dsb2 disulfide bond isomerases obtainable from any gram positive organism. In a preferred embodiment, the gram-positive organism is *Bacillus*. In another preferred embodiment, the gram-positive organism if from *B. subtilis*. As used herein, the phrase, "*B. subtilis* Dsb1" or "*B. subtilis* disulfide bond isomerase 1" refers to the amino acid sequence shown in FIG. 1. As used herein, the phrase, "*B. subtilis* Dsb2" or "*B. subtilis* disulfide bond isomerase 2" refers to the amino acid sequence shown in FIG. 7. The present invention encompasses amino acid variants of *B. subtilis* Dsb1 and Dsb2 disclosed in FIGS. 1 and 7, respectively, that are able to modulate protein folding and/or secretion alone or in combination with other molecular factors, such as secretion factors.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "*B. subtilis* polynucleotide homolog" or "polynucleotide homolog" as used herein refers to a polynucleotide that has at least 80%, at least 90% and at least 95% identity to *B. subtilis* Dsb1 or Dsb2 or which is capable of hybridizing to *B. subtilis* Dsb1 or Dsb2 under conditions of high stringency and which encodes an amino acid sequence that is able to modulate secretion of the gram-positive microorganism from which it is derived. Modulate as used herein refers to the ability of a disulfide bond isomerase to alter the secretion machinery such that secretion of proteins is altered.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases, cellulases, amylases, other carbohydrases, reductases and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrates such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein, or a variant thereof, re-introduced in a recombinant form. In another embodiment, the host cell produces the homologous protein.

DETAILED DESCRIPTION OF THE PREFERRED EMBODIMENTS

The present invention provides novel gram-positive microorganism disulfide bond isomerases Dsb1 and Dsb2 and methods that can be used in gram-positive microorganisms to ameliorate the bottleneck to secretion of proteins in their native or naturally occurring conformation, in particular when the proteins are recombinantly introduced and overexpressed by the host cell. The present invention provides the disulfide bond isomerase Dsb1 and Dsb2 derived from *Bacillus subtilis*.

I. Dsb1 and Dsb2 Nucleic Acid and Amino Acid Sequences
    Nucleic Acid

The Dsb1 and Dsb2 polynucleotides having the sequence as shown in FIGS. 1 and 7, respectively, encode the *Bacillus subtilis* disulfide bond isomerase Dsb1 and Dsb2. The *Bacillus subtilis* Dsb1 and Dsb2 were identified via a FASTA search of *Bacillus subtilis* uncharacterized translated genomic sequences using an *E. coli* disulfide bond isomerase. The present invention provides gram-positive Dsb1 and Dsb2 polynucleotides which may be used alone or together with factors in a gram-positive microorganism for the purpose of increasing the secretion of desired heterologous or homologous proteins or polypeptides in their native or naturally occurring conformation.

The present invention encompasses novel *B. subtilis* Dsb1 and Dsb2 polynucleotide homologs encoding gram-positive microorganism Dsb1 and Dsb2 which have at least 80%, or at least 90% or at least 95% identity to *B. subtilis* Dsb1 and Dsb2 as long as the homolog encodes a protein that is able to function by modulating secretion in a gram-positive microorganism. As will be understood by the skilled artisan, due to the degeneracy of the genetic code, a variety of polynucleotides, i.e., Dsb1 and Dsb2 polynucleotide variants, can encode the *Bacillus subtilis* disulfide bond isomerase s Dsb1 and Dsb2. The present invention encompasses all such polynucleotides.

Gram-positive microorganism polynucleotide homologs of *B. subtilis* Dsb1 and Dsb2 can be identified through nucleic acid hybridization of gram-positive microorganism nucleic acid of either genomic of cDNA origin. The polynucleotide homolog sequence can be detected by DNA-DNA or DNA-RNA hybridization or amplification using *B. subtilis* Dsb1 and Dsb2 probes, portions or fragments disclosed in the nucleotide sequence shown in the Figures. Accordingly, the present invention provides a method for the detection of gram positive microorganism Dsb1 and Dsb2 polynucleotide homologs which comprises hybridizing a nucleic acid sample with part or all of a nucleic acid sequence from *B. subtilis* Dsb1 and Dsb2.

Also included within the scope of the present invention are gram-positive microorganism Dsb1 and Dsb2 polynucleotide homologs that are capable of hybridizing to part or all of *B. subtilis* Dsb1 and Dsb2 under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) *Dictionary of Biotechnology*, Stockton Press, New York N.Y.).

The process of amplification as carried out in polymerase chain reaction (PCR) technologies is described in Dieffenbach C W and G S Dveksler (1995, *PCR Primer, a Laboratory Manual*, Cold Spring Harbor Press, Plainview N.Y.). A nucleic acid sequence of at least about 10 nucleotides and as many as about 60 nucleotides from the Dsb1 and Dsb2 nucleotide sequence of FIG. 1, preferably about 12 to 30 nucleotides, and more preferably about 20–25 nucleotides can be used as a probe or PCR primer.

Amino Acid Sequences

The *B. subtilis* Dsb1 and Dsb2 polynucleotide as shown in FIGS. 1 and 7 encode *B. subtilis* Dsb1 and Dsb2. The present invention encompasses novel gram positive microorganism amino acid variants of the *B. subtilis* Dsb1 and Dsb2 amino acid sequences that are at least 80% identical, at least 90% identical and at least 95% identical to *B. subtilis* Dsb1 and Dsb2 as long as the amino acid sequence variant is able to function in a gram-positive microorganism.

The *B. subtilis* Dsb1 and Dsb2 were discovered upon a FASTA amino acid search of translated *B. subtilis* genomic DNA sequences vs. An *E.coli* disulfide bond isomerase amino acid sequence (FASTA search Release 1.0, released on Jun. 11, 1997) parameters being Scoring matrix: GenRunData: blosum50.cmp; variable pamfactor used; Gap creation penalty: 12; and Gap extension penalty: 2). Amino acid alignments are shown in FIGS. 2 and 3. The hydrophilicity profile for *B. subtilis* Dsb1 and Dsb2, shown in FIGS. 5 and 6, show potential membrane spanning regions.

II. Expression Systems

The present invention provides expression systems for the enhanced production and secretion of desired heterologous or homologous proteins in gram-positive microorganisms.

a. Coding Sequences

In the present invention, the vector comprises at least one copy of nucleic acid encoding a gram-positive microorganism Dsb1 and/or Dsb2and preferably comprises multiple copies. In a preferred embodiment, the gram-positive microorganism is *Bacillus*. In another preferred embodiment, the gram-positive microorganism is *Bacillus subtilis*. In a preferred embodiment, polynucleotides which encode *B. subtilis* Dsb1 and Dsb2, or fragments thereof, or fusion proteins or polynucleotide homolog sequences that encode amino acid variants of Dsb1 and Dsb2, may be used to generate recombinant DNA molecules that direct the expression of Dsb1 or Dsb2, or amino acid variants thereof, respectively, in gram-positive host cells. In a preferred embodiment, the host cell belongs to the genus *Bacillus*. In another preferred embodiment, the host cell is *B. subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered gram positive Dsb1 and Dsb2 polynucleotide sequences which may be used in accordance with the invention include deletions, insertions or substitutions of different nucleotide residues resulting in a polynucleotide that encodes the same or a functionally equivalent Dsb1 and Dsb2 homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring gram positive Dsb1 and Dsb2.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent gram-positive Dsb1 or Dsb2 variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The Dsb1 and Dsb2 polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a Dsb1 and Dsb2 polynucleotide may be ligated to a heterologous sequence to encode a fusion protein. A fusion protein may also be engineered to contain a cleavage site located between the Dsb1 and Dsb2 nucleotide sequence and the heterologous protein sequence, so that the Dsb1 and Dsb2 protein may be cleaved and purified away from the heterologous moiety.

b. Vector Sequences

Expression vectors used in expressing the disulfide bond isomerases of the present invention in gram-positive microorganisms comprise at least one promoter associated with a gram-positive Dsb1 and Dsb2, which promoter is functional in the host cell. In one embodiment of the present invention, the promoter is the wild-type promoter for the selected disulfide bond isomerase and in another embodiment of the present invention, the promoter is heterologous to the disulfide bond isomerase, but still functional in the host cell.

Additional promoters associated with heterologous nucleic acid encoding desired proteins or polypeptides may be introduced via recombinant DNA techniques. In one embodiment of the present invention, the host cell is capable of overexpressing a heterologous protein or polypeptide and nucleic acid encoding one or more disulfide bond isomerase(s) is(are) recombinantly introduced. In one preferred embodiment of the present invention, nucleic acid encoding Dsb1 or Dsb2 is stably integrated into the microorganism genome. In another embodiment, the host cell is engineered to overexpress a disulfide bond isomerase of the present invention and nucleic acid encoding the heterologous protein or polypeptide is introduced via recombinant DNA techniques. The present invention encompasses gram-positive host cells that are capable of overexpressing other disulfide bond isomerase s known to those of skill in the art, including but not limited to, SecA, SecY, SecE or other disulfide bond isomerases known to those of skill in the art or identified in the future.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

c. Transformation

In one embodiment of the present invention, nucleic acid encoding at least one gram-positive disulfide bond isomerase of the present invention is introduced into a gram-positive host cell via an expression vector capable of replicating within the host cell. Suitable replicating plasmids for *Bacillus* are described in Molecular Biological Methods for *Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a gram-positive micro-organism Dsb1 and/or Dsb2 is stably integrated into the microorganism genome. Preferred gram-positive host cells are from the genus *Bacillus*. Another preferred gram-positive host cell is *B. subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., *Plasmid* 2:555–571 (1979); Haima et al., *Mol. Gen. Genet.* 223:185–191 (1990); Weinrauch et al., *J. Bacteriol.* 154(3):1077–1087 (1983); and Weinrauch et al., *J. Bacteriol.* 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) *Mol. Gen. Genet* 168:111–115; for *B. megaterium* in Vorobjeva et al., (1980) FEMS Microbiol. Letters 7:261–263; for *B. amyloliquefaciens* in Smith et al., (1986) Appl. and Env. Microbiol. 51:634; for *B. thuringiensis* in Fisher et al., (1981) Arch. Microbiol. 139:213–217; for *B. sphaericus* in McDonald (1984) J. Gen. Microbiol. 130:203; and *B. larvae* in Bakhiet et al., (1985) 49:577. Mann et al., (1986, Current Microbiol. 13:131–135) report on transformation of *Bacillus* protoplasts and Holubova, (1985) Folia Microbiol. 30:97) disclose methods for introducing DNA into protoplasts using DNA containing liposomes.

III. Identification of Transformants

Although the presence/absence of marker gene expression suggests that the gene of interest is also present, its presence and expression should be confirmed. For example, if the nucleic acid encoding Dsb1 and Dsb2 is inserted within a marker gene sequence, recombinant cells containing the insert can be identified by the absence of marker gene function. Alternatively, a marker gene can be placed in tandem with nucleic acid encoding the disulfide bond isomerase under the control of a single promoter. Expression of the marker gene in response to induction or selection usually indicates expression of the disulfide bond isomerase as well.

Alternatively, host cells which contain the coding sequence for a disulfide bond isomerase and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the Dsb1 or Dsb2 polynucleotide sequence can be detected by DNA-DNA or DNA-RNA hybridization or amplification using probes, portions or fragments derived from the *B. subtilis* Dsb1 or Dsb2 polynucleotide.

IV. Secretion Assays

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

V. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a disulfide bond isomerase of the present invention will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

VI. Uses of the Present Invention

Genetically Engineered Host Cells

The present invention provides genetically engineered host cells comprising nucleic acid encoding gram-positive microorganism Dsb1 and/or Dsb2. In one preferred embodiment, the nucleic acid is stably integrated into the microorganism. In another preferred embodiment, the Dsb1 and/or Dsb2 have the nucleic acid sequence shown in FIGS. 1 and 7, respectively. The host cell may comprise nucleic acid encoding additional secretions factors.

The preferred embodiment, the host cell is genetically engineered to produce a desired protein or polypeptide. In a preferred embodiment, the host cell is a *Bacillus*. In another preferred embodiment, the host cell is *Bacillus subtilis*.

In an alternative embodiment, a host cell is genetically engineered to produce a gram-positive Dsb1 or Dsb2.

Polynucleotides

*B. subtilis* Dsb1 or Dsb2 polynucleotides, or any part thereof, provides the basis for detecting the presence of gram-positive microorganism polynucleotide homologs through hybridization techniques and PCR technology.

Accordingly, one aspect of the present invention is to provide for nucleic acid hybridization and PCR probes derived from B. subtilis Dsb1 or Dsb2 which can be used to detect other gram positive microorganism polynucleotide sequences, including genomic and cDNA sequences.

EXAMPLE I

Preparation of a Genomic Library

The following example illustrates the preparation of a *Bacillus* genomic library.

Genomic DNA from *Bacillus* cells is prepared as taught in Current Protocols In Molecular Biology vol. 1, edited by Ausubel et al., John Wiley & Sons, Inc. 1987, chapter 2. 4.1. Generally, *Bacillus* cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the *Bacillus* genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested *Bacillus* genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram-positive Microorganism Disulfide Bond Isomerase

The following example describes the detection of gram-positive microorganism Dsb1 or Dsb2.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from Dsb1 or Dsb2.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologs of *B. subtilis* Dsb1 or Dsb2. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

The invention claimed is:

1. An expression vector comprising a nucleic acid encoding at least one *Bacillus subtilis* disulfide bond isomerase (Dsb) having an amino acic sequence selected from the group consisting of SEQ ID NOS:2 and 5, wherein said nucleic acid encoding disulfide bond isomerase is under the control of expression signals that overexpress said disulfide bond isomerase in a Gram-positive bacterium.

2. The expression vector of claim 1, wherein said Gram-positive bacterium is a member of the genus *Bacillus*.

3. The expression vector of claim 2, wherein said member of the genus *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lentus,* and *B. thuringiensis*.

4. A Gram positive bacterial host cell comprising the expression vector of claim 1.

5. The Gram-positive bacterial host cell of claim 4, wherein said host cell is a member of the genus *Bacillus*.

6. The Gram-positive bacterial host cell of claim 5, wherein said member of the genus *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lentus* and *B. thuringiensis*.

7. The Gram-positive bacterial host cell of claim 5, wherein said host cell expresses at least one heterologous protein.

8. The Gram-positive bacterial host cell of claim 7, wherein said heterologous protein is selected from the group consisting of hormones, enzymes, growth factors, and cytokines.

9. The Gram-positive bacterial host cell of claim 8, wherein said heterologous protein is an enzyme.

10. The Gram-positive bacterial host cell of claim 9, wherein said enzyme is selected from the group consisting of proteases, carbohydrases, reductases, lipases, isomerases, transferases, kinases, and phosphatases.

11. The expression vector of claim 1, comprising at least one nucleic acid having a nucleic acid sequence selected from the group consisting of SEQ ID NOS:1 and 4.

12. A Gram positive bacterial host cell comprising the expression vector of claim 11.

* * * * *

SEQUENCE LISTING

```
<160> NUMBER OF SEQ ID NOS: 5
<210> SEQ ID NO 1
<211> LENGTH: 444
<212> TYPE: DNA
<213> ORGANISM: Bacillus subtilis

<400> SEQUENCE: 1
atgaatacaa gatatgtaaa atcattttt  ttattactgt ttttctctc  tttctttggc   60 acaatggcta gtttattcta cagtgagatc atgcatttca aaccatgtgt tctatgttgg  120
tatcaaagaa tatttctata tcctatacct attatcttac taataggctt attaaaaaaa  180
gatcttaatt cgatatttta tgttgttttc ctttcatcaa ttggattgat tattgcgttt  240
tatcattata ttatccaact tacacaaagc aaaagtgtcg tatgtgaaat tggaaccaac  300
agctgcgcaa aaattgaagt agagtatcta ggctttatta cattacccett aatgagttca  360 gtatgttttg cattgatatt tggtatagga ctgaaattaa ttatcaaaag caagaaatta  420
aaacaaaatc aacatgtata taat                                         444

<210> SEQ ID NO 2
<211> LENGTH: 148
<212> TYPE: PRT
<213> ORGANISM: Bacillus subtilis

<400> SEQUENCE: 2

Met Asn Thr Arg Tyr Val Lys Ser Phe Phe Leu Leu Leu Phe Phe Leu
  1               5                  10                  15

Ser Phe Phe Gly Thr Met Ala Ser Leu Phe Tyr Ser Glu Ile Met His
             20                  25                  30

Phe Lys Pro Cys Val Leu Cys Trp Tyr Gln Arg Ile Phe Leu Tyr Pro
         35                  40                  45

Ile Pro Ile Ile Leu Leu Ile Gly Leu Leu Lys Lys Asp Leu Asn Ser
     50                  55                  60

Ile Phe Tyr Val Val Phe Leu Ser Ser Ile Gly Leu Ile Ile Ala Phe
 65                  70                  75                  80

Tyr His Tyr Ile Ile Gln Leu Thr Gln Ser Lys Ser Val Val Cys Glu
                 85                  90                  95

Ile Gly Thr Asn Ser Cys Ala Lys Ile Glu Val Glu Tyr Leu Gly Phe
            100                 105                 110

Ile Thr Leu Pro Leu Met Ser Ser Val Cys Phe Ala Leu Ile Phe Gly
        115                 120                 125

Ile Gly Leu Lys Leu Ile Ile Lys Ser Lys Lys Leu Lys Gln Asn Gln
    130                 135                 140

His Val Tyr Asn
145

<210> SEQ ID NO 3
<211> LENGTH: 176
```

-continued

```
<212> TYPE: PRT
<213> ORGANISM: Bacillus subtilis

<400> SEQUENCE: 3

Met Leu Arg Phe Leu Asn Gln Cys Ser Gln Gly Arg Gly Ala Trp Leu
1               5                   10                  15

Leu Met Ala Phe Thr Ala Leu Ala Leu Glu Leu Thr Ala Leu Trp Phe
            20                  25                  30

Gln His Val Met Leu Leu Lys Pro Cys Val Leu Cys Ile Tyr Glu Arg
        35                  40                  45

Cys Ala Leu Phe Gly Val Leu Gly Ala Ala Leu Ile Gly Ala Ile Ala
    50                  55                  60

Pro Lys Thr Pro Leu Arg Tyr Val Ala Met Val Ile Trp Leu Tyr Ser
65                  70                  75                  80

Ala Phe Arg Gly Val Gln Leu Thr Tyr Glu His Thr Met Leu Gln Leu
                85                  90                  95

Tyr Pro Ser Pro Phe Ala Thr Cys Asp Phe Met Val Arg Phe Pro Glu
            100                 105                 110

Trp Leu Pro Leu Asp Lys Trp Val Pro Gln Val Phe Val Ala Ser Gly
        115                 120                 125

Asp Cys Ala Glu Arg Gln Trp Asp Phe Leu Gly Leu Glu Met Pro Gln
    130                 135                 140

Trp Leu Leu Gly Ile Phe Ile Ala Tyr Leu Ile Val Ala Val Leu Val
145                 150                 155                 160

Val Ile Ser Gln Pro Phe Lys Ala Lys Lys Arg Asp Leu Phe Gly Arg
                165                 170                 175

<210> SEQ ID NO 4
<211> LENGTH: 414
<212> TYPE: DNA
<213> ORGANISM: Bacillus subtilis

<400> SEQUENCE: 4
atgaaaaata gaatcgtatt tttatatgct tcctgggttg tggctcttat cgctatgctg     60
ggcagcctgt atttcagtga atcagaaag tttattccat gtgaactgtg ctggtaccag    120
cgtatcctca tgtatccgct cgtcctgatt ttaggcatcg ccacctttca aggggacaca    180
cgagtgaaaa aatatgtgct cccgatggcg attattgggg cattcatttc gatcatgcat    240
tacttagagc aaaaagtgcc cggctttagc ggcattaagc catgtgtcag cggcgtgccg    300
tgctcgggcc aatatattaa ctggtttggt tttattacga ttccattcct ggccctgatt    360
gcttttatcc tgattatcat ttttatgtgc ctgctgaaag gcgaaaaatc tgaa          414

<210> SEQ ID NO 5
<211> LENGTH: 138
<212> TYPE: PRT
<213> ORGANISM: Bacillus subtilis

<400> SEQUENCE: 5

Met Lys Asn Arg Ile Val Phe Leu Tyr Ala Ser Trp Val Val Ala Leu
1               5                   10                  15

Ile Ala Met Leu Gly Ser Leu Tyr Phe Ser Glu Ile Arg Lys Phe Ile
            20                  25                  30

Pro Cys Glu Leu Cys Trp Tyr Gln Arg Ile Leu Met Tyr Pro Leu Val
        35                  40                  45

Leu Ile Leu Gly Ile Ala Thr Phe Gln Gly Asp Thr Arg Val Lys Lys
    50                  55                  60
```

```
-continued

Tyr Val Leu Pro Met Ala Ile Ile Gly Ala Phe Ile Ser Ile Met His
65              70              75              80

Tyr Leu Glu Gln Lys Val Pro Gly Phe Ser Gly Ile Lys Pro Cys Val
            85              90              95

Ser Gly Val Pro Cys Ser Gly Gln Tyr Ile Asn Trp Phe Gly Phe Ile
        100             105             110

Thr Ile Pro Phe Leu Ala Leu Ile Ala Phe Ile Leu Ile Ile Ile Phe
        115             120             125

Met Cys Leu Leu Lys Gly Glu Lys Ser Glu
    130             135
```